US00PP36188P2

(12) United States Plant Patent
Hansen

(10) Patent No.: US PP36,188 P2
(45) Date of Patent: Oct. 8, 2024

(54) ***CLEMATIS* PLANT NAMED 'Stand by Me Pink'**

(50) Latin Name: ***Clematis* hybrid**
Varietal Denomination: Stand by Me Pink

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 18/445,588

(22) Filed: Nov. 7, 2023

(51) Int. Cl.
*A01H 5/02* (2018.01)
*A01H 6/72* (2018.01)

(52) U.S. Cl.
USPC ..... Plt./228
CPC ..... *A01H 6/72* (2018.05)

(58) Field of Classification Search
USPC ..... Plt./228
CPC ..... A01H 5/02
See application file for complete search history.

*Primary Examiner* — Kent L Bell

(57) ABSTRACT

A new hybrid Clematis plant, 'Stand by Me Pink', of compact, medium height, non-vining habit with ovate leaves and dark purple buds producing nodding flowers with typically four reflexed tepals of pinkish-lavender beginning late May to June and reblooming through late summer.

2 Drawing Sheets

Botanical denomination: Clematis hybrid.
Cultivar designation: 'Stand by Me Pink'.

STATEMENT REGARDING PRIOR DISCLOSURES UNDER 37 CFR 1.77(b)(6)

The first public disclosure of the claimed plant, in the form of a sale, was made by Walters Gardens, Inc. on Sep. 25, 2023, to Vesey Seeds Ltd. Prior to that, on Dec. 1, 2022, the claimed plant was displayed with a photograph and brief description in a website operated by Walters Gardens, Inc., and on May 19, 2023, as a photograph and brief description in the 2023-2024 Catalog by Walters Gardens, Inc., who obtained the plant and all information relating thereto, from the inventor. No plants of Clematis 'Stand by Me Pink' were sold or offered for sale in this country or anywhere in the world, nor has any disclosure of the new plant been made more than one year prior to the filing date of this application, and such sale or disclosure within one year was either derived directly or indirectly from the inventor.

BACKGROUND OF THE INVENTION

The present invention relates to a new and distinct plant of herbaceous type clematis. The new plant is the result of a single seedling selection from a cross between Clematis 'Stand by Me' U.S. Plant Pat. No. 30,556 as the female parent and the male parent was an unnamed proprietary pink-flowering selection of *C. integrifolia* (not patented). The cross was performed on Jun. 18, 2013, by the inventor at a wholesale perennial nursery in Zeeland, Mich., USA. The new plant passed the original evaluation in the summer of 2015 at the same nursery in Zeeland, Mich., and was assigned the breeder code 13-31-11 during these remaining trials. The new plant was selected from among many other seedlings growing at the same nursery in Zeeland, Mich. which met the rigorous criteria of excellent flowers, foliage, and habit established as breeding goals.

'Stand by Me Pink' has been asexually propagated since 2018 by shoot tip cuttings at the same nursery in Zeeland, Mich. The resultant asexually propagated plants have remained stable and exhibit identical characteristics as the original plant in successive generations.

BRIEF SUMMARY OF THE INVENTION

'Stand by Me Pink' differs from all other Clematis known to the applicant. The nearest known cultivars are: *Clematis* 'Rain Dance' U.S. Plant Pat. No. 33,875, 'Stand by Me Lavender' U.S. Plant Pat. No. 34,275, 'Violet Stardust' U.S. Plant Pat. No. 30,555, *Clematis x durandii* 'Pallida' (not patented).

'Rain Dance' has a taller habit, with larger, flatter, and more upward-facing indigo-blue flowers and tri-lobed foliage. 'Violet Stardust' has a taller habit with smaller more numerous flowers that are more violet-blue. 'Pallida' and other *x durandii* plants known to the Inventor are not as tall and not as floriferous with lavender-purple flowers. 'Stand by Me Lavender' has a similar habit with more dusty lavender flowers.

The female parent, 'Stand by Me', has a similar habit with foliage having a more purplish-bronze cast to the back of the foliage when young and more bell-shaped flowers with violet-blue tepals. The male parent has a shorter habit, the flowers are smaller with narrower petals that are more pinkish than the new plant, and the foliage is narrower.

'Stand by Me Pink' differs from all clematis known to the inventor in the following combined traits:

1. The foliage is ovate and glabrous above and below;
2. Nodding flowers typically having four pinkish-lavender tepals per flower begin in late May to June with rebloom through the late summer;
3. The plant habit is intermediate in height and benefits from stakes or other nearby plants when mature.

BRIEF DESCRIPTION OF THE DRAWINGS

The photographs of the new plant demonstrate the overall appearance in a display garden at a wholesale perennial nursery in Zeeland, Mich., USA. The colors are as accurate as reasonably possible with color reproductions. Some slight variations of color may occur as a result of lighting quality, intensity, wavelength, direction, or reflection.

DETAILED BOTANICAL DESCRIPTION

Figure 1:
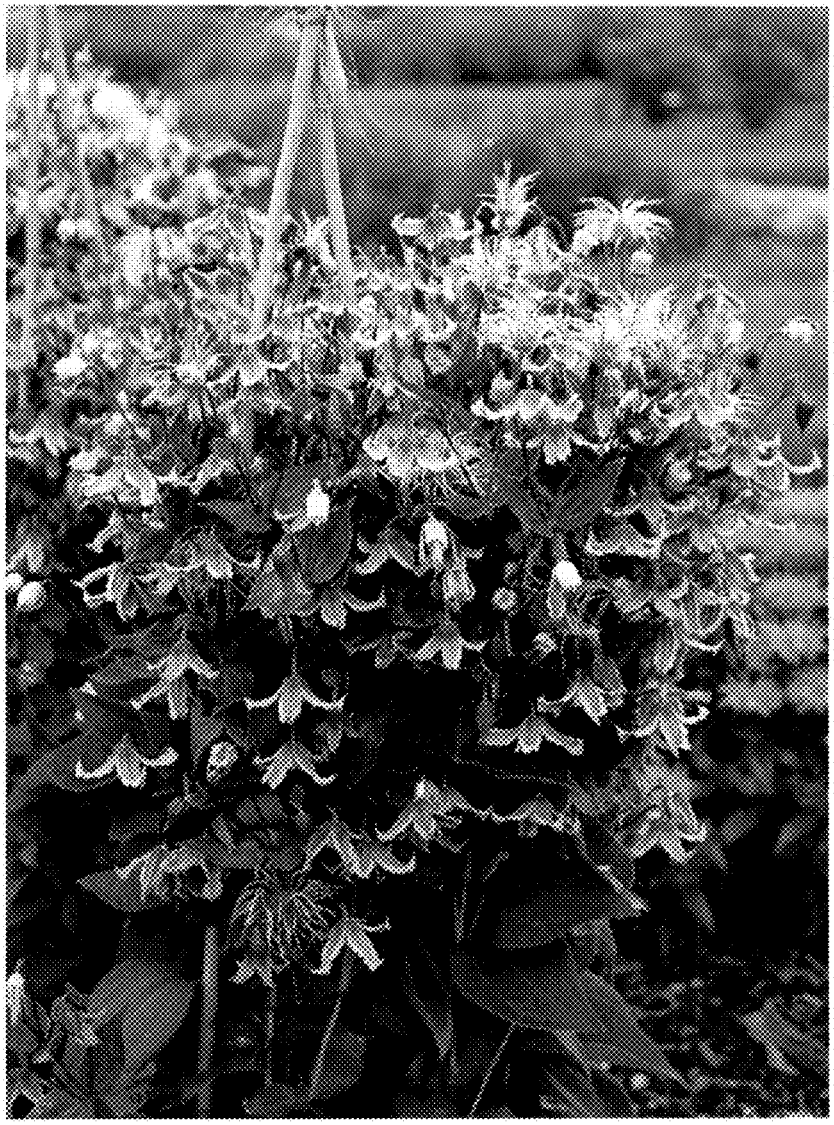
FIG. 1 shows a three-year-old plant in peak flower supported by stakes.
Figure 2:
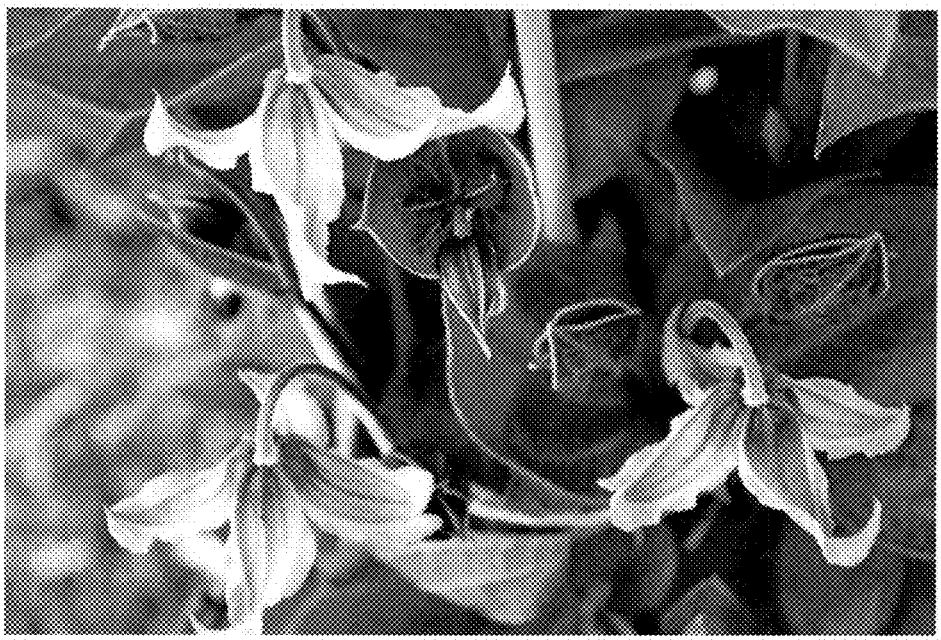
FIG. 2 shows a close-up of the flowers and buds from above.
Figure 3:
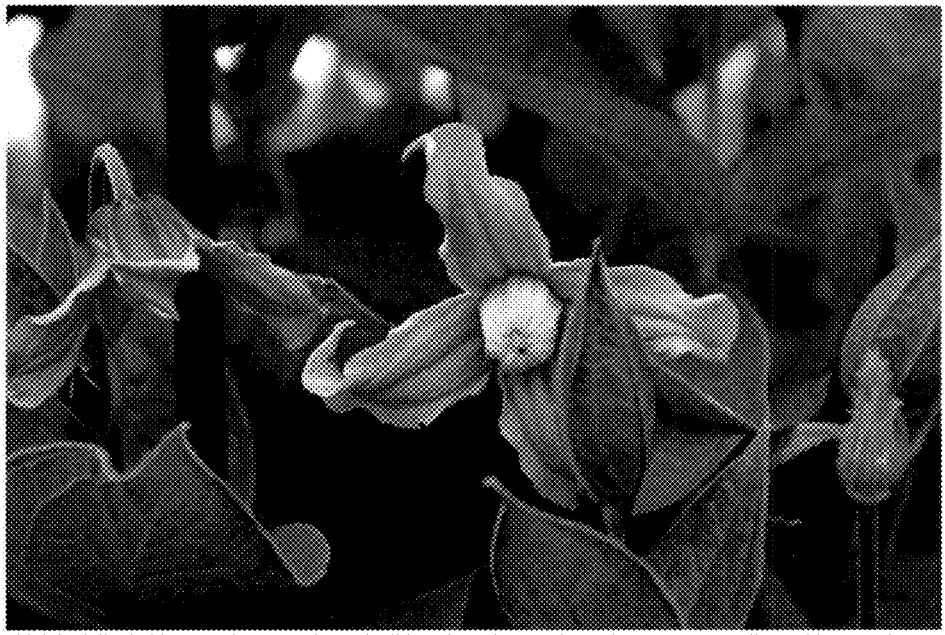
FIG. 3 shows a close-up of the flowers from below and the side.

The following description is based on a five-year-old plant growing in a full-sun trial garden with supplemental water and fertilizer at a wholesale perennial nursery in Zeeland, Michigan, USA. The new plant has not been grown under all possible environments and may phenotypically appear different under different conditions such as light, temperatures, fertilizer, and water, without any difference in genotype. The color descriptions are from the 2015 edition of The Royal Horticultural Society Colour Chart except where common dictionary terms are used.

*Parentage*.—the female (seed parent) is 'Stand by Me'; the male (pollen parent) is a proprietary unnamed pink flowering selection of C. *integrifolia*.

*Plant habit*.—winter-hardy, herbaceous perennial of semi-woody stems producing upright spreading habit, dying to the ground each winter, flowering on new growth; to about 107 cm tall in flower and spreading to about 90 cm across about 40 cm above the soil; width of the stem portion to about 13 cm across at base.

*Roots*.—coarse; branched; tan to light brown in color depending on soil type; color nearest RHS 165C.

*Growth rate*.—rapid, finishing in a four-liter container in about 8 to 10 weeks from a one-year-old vernalized plant.

*Stems*.—to about 35 per plant; cylindrical with longitudinal carina; sparsely micro-puberulent; branched in upper nodes; to about 119 cm long and 5 mm diameter at base; flowering in upper one half to one-third of the plant.

*Stem color*.—older proximal stems nearest RHS N200D with carina nearest RHS N187A, younger proximal stems between RHS '178A and RHS 177B; distal stems nearest RHS 137A with carina between RHS 146D and RHS 145C.

*Branches*.—initially erect, parallel main stem; with longitudinal carina; sparsely micro-puberulent; to about 30 cm long and 2.5 mm diameter at base.

*Branch color*.—stems nearest RHS 137A with carina between RHS 146D and RHS 145C.

*Nodes*.—about 9 to 11 per stem, and to about 7 mm across.

*Node color*.—variable, on mature stems nearest N186A and nearest RHS 200A, on young stems nearest RHS 145A in lower light and nearest RHS 187B on young stems in high light exposure.

*Foliage*.—opposite; simple; ovate; apex acute, base rounded, margin entire, glabrous adaxial and abaxial; newly expanded foliage is upright, maturing to flat and horizontal.

*Leaf blade size: variable*.—simple—to about 13 cm long and 9 cm wide near base.

*Leaf color*.—young emerging leaves adaxial surface nearest RHS 146B with occasional blush to solid portions of nearest RHS 187A, abaxial surface nearest RHS 146B with occasional undertone of nearest RHS 187A; proximal mature leaves adaxial surface nearest RHS 137A, abaxial surface nearest RHS 147B.

*Petiole*.—sessile in proximal leaves; in distal leaves—concavo-convex; glabrous; to 3 cm long and 2 mm wide at base.

*Petiole color*.—adaxial between RHS 138A and RHS 138B and abaxial nearest RHS 138B.

*Veins*.—bi-nerved; convergent; glabrous adaxial and abaxial; sunken adaxial; costate abaxial.

*Vein color*—adaxial leaves nearest RHS 146C; abaxial leaves midrib and primary veins nearest RHS 147C and secondary veins nearest 137A.

*Inflorescence*.—flowers solitary; at nodes; flowering portion in distal one-half to one-third of the plant.

*Flower attitude*.—buds upright, flowers downwardly.

*Flower fragrance*.—none detected.

*Flower period*.—late May to June with rebloom through late summer; individual flowers remaining effective in flower for about 6 to 8 days.

*Peduncle*.—cylindrical with longitudinal carina; micro-puberulent; to about 16 cm long and 3 mm in diameter on initial center flowers, about 5 cm long and 2 mm diameter on side branch flowers, average 7.8 cm long and 2.5 mm diameter on center and side branch flowers.

*Peduncle attitude*.—upright.

*Peduncle color*.—nearest RHS 177A proximally and nearest RHS N187A distally.

*Buds one day prior to opening*.—conical with narrowly acute apex, and cordate to rounded base; glabrous, with carina along tepal unions ciliolate; about 22 mm long and 9 mm diameter.

*Bud color*.—basal one-third to one-half nearest RHS 79A transitioning to nearest RHS N79B distally.

*Flower*.—solitary; perfect; single; incomplete; campanulate, cruciform; actinomorphic; about 33 mm across at tepal apices and 22 mm deep.

*Flower aspect*.—outwardly.

*Tepals*.—typically, four; lanceolate; apex acute, apiculate, recurved; truncate base; typically, tri-nerved with midrib and one pair of main veins, deeply furrowed in three main veins; margins entire proximally, distal one-half of margin erosulate; adaxial glabrous and matte; micro-puberulent abaxial between outer vein pair and margin, glabrous and matte between outer main vein pair and midrib; about 23 mm long and 9 mm wide in middle; self-cleaning;

*Tepal color*.—young and mature adaxial nearest RHS 86D outside of main veins and nearest RHS 86B inside main veins, basal 2 mm portion nearest RHS 93A; abaxial mature longitudinal center between RHS 79C and RHS 79B with basal 2 mm nearest RHS 79B, margins outside main veins nearest RHS N88C, and midrib and main veins nearest RHS 79A; young abaxial distally nearest RHS N80D, close to the base nearest RHS N81B, and with basal 2 mm between RHS 77A and RHS 77B, proximal veins nearest RHS N81B and distally becoming nearest RHS N81C.

*Petals and sepals*.—not present.

*Androecium*.—about 60, in multiple rows; flattened dorsal-ventrally, adaxial and abaxial pubescent distal half, glabrous proximal half; total 11 mm long and 2 mm wide. Filaments: flattened; pubescent abaxial, glabrous adaxial, margin ciliate; about 8 mm long and 2 mm wide and about 0.2 mm thick; color young adaxial and abaxial nearest RHS 191D, mature adaxial nearest RHS 4B distally with proximal 2 to 3 mm nearest RHS 4D, mature abaxial proximal two-thirds nearest RHS 191D, distal one-third nearest RHS 7B. Anthers: basifixed; longitudinal; ellipsoidal; glabrous; introrse; to about 3.5 mm long and 1 mm diameter, decreasing toward flower axis; color nearest RHS 4D. Pollen:abundant; powdery; color nearest RHS 11D.

*Gynoecium*.—about 40; internal to androecium; to 10 mm long. Style: terete to tapered; about 7 mm long and 0.8 mm diameter; pilose to sericeous; color nearest RHS 195D covered in silvery hairs. Stigma: cylindrical; about 3 mm long and 0.5 mm diameter; color nearest RHS 155C. Torus: semi-dome shaped; about 4 mm diameter across at the base and 3 mm tall; color nearest RHS 160C when young and nearest RHS N199B at maturity.

*Reproductive structures*.—Fruit: produced in globose plumose head, to about 5 cm diameter and 5 cm tall; seeds with plumose tails curved around equal distance above and below torus. Seed: abundant, about 50 to 60 per head; flattened achene with style persistent as plumose tail; hairs adpressed becoming antrorse as maturing and at nearly 90-degree angle to style when mature, extending about 4 mm long; tail portion to 46 mm long; pubescent achene base 5 mm long, 3.5 mm wide and 1 mm thick. Seed color as mature: plumose feather tail nearest RHS 199D, achene basal one-half nearest RHS 166D, and distally nearest RHS N199B.

*Culture*.—*Clematis* 'Stand by Me Pink' grows best in full sun with ample moisture, good drainage, and mulch. The new plant is cold hardy from USDA zone 3 to at least zone 8.

*Disease and pest tolerance*.—Resistant to clematis wilt, *Ascochyta clematidina*. Pest and disease resistance and tolerance outside of that normal for *Clematis* is not known at this time.

It is claimed:

1. A new and distinct ornamental *Clematis* plant named 'Stand by Me Pink' as herein described and illustrated.

* * * * *